(12) United States Patent
van der Eerden et al.

(10) Patent No.: US 6,998,398 B2
(45) Date of Patent: Feb. 14, 2006

(54) SOLID SALTS OF BENZAZEPINE COMPOUNDS AND PHARMACEUTICAL COMPOSITIONS CONTAINING THEM

(75) Inventors: Joris A. van der Eerden, Weesp (DE); Paulus P. G. de Jong, Weesp (DE); Paulus F. C. van der Meij, Weesp (DE)

(73) Assignee: Solvay Pharmaceuticals BV, Weesp (NL)

( * ) Notice: Subject to any disclaimer, the term of this patent is extended or adjusted under 35 U.S.C. 154(b) by 0 days.

(21) Appl. No.: 10/890,392

(22) Filed: Jul. 14, 2004

(65) Prior Publication Data

US 2005/0038012 A1 Feb. 17, 2005

Related U.S. Application Data

(63) Continuation of application No. PCT/EP03/00515, filed on Jan. 15, 2003.

(30) Foreign Application Priority Data

Jan. 16, 2002 (EP) ................... 02075621
Jan. 17, 2002 (NL) ................... 1019762

(51) Int. Cl.
C07D 487/00 (2006.01)
A61K 38/05 (2006.01)
A61P 9/00 (2006.01)
(52) U.S. Cl. .................. 514/212.07; 540/523
(58) Field of Classification Search ............... 540/523; 514/212.07

See application file for complete search history.

(56) References Cited

U.S. PATENT DOCUMENTS 5,783,573 A 7/1998 Rozsa et al.

FOREIGN PATENT DOCUMENTS

| EP | 0733642 | 9/1996 |
|---|---|---|
| EP | 0830863 | 3/1998 |
| WO | WO 00/48601 | 8/2000 |
| WO | WO 01/03699 | 1/2001 |

OTHER PUBLICATIONS

Zeev B. Alfassi, et al., "Solventing out of Electrolytes form their Aqueous Solution", AIChE Journal, Sep. 1984, pp. 874-876, vol. 30, No. 5.

Jerzy Mydlarz, et al., "Solubility and Density Isotherms for Potassium Sulfate-Water-2-Propanol", J. Chem. Eng. Data, 1989, pp. 124-126, 34, American Chemical Society.

J. W. Mullin, et al., "Potassium Sulphate Precipitation from Aqueous Solution by Salting-out with Acetone", Chem. Eng. Process., 1989, pp .93-99, 26, Elsevier Sequoia, The Netherlands.

Primary Examiner—Bruck Kifle
(74) Attorney, Agent, or Firm—Crowell & Moring LLP

(57) ABSTRACT

Pharmaceutically acceptable metal salts of compounds of formula (I):

in which $R_1$ is selected from the group consisting of $(C_1-C_6)$alkoxy $(C_1-C_6)$alkyl which may be substituted with $(C_1-C_6)$alkoxy, phenyl-$(C_1-C_6)$-alkyl and/or phenyloxy-$(C_1-C_6)$-alkyl group in which any phenyl group may be substituted with $(C_1-C_6)$alkyl, $(C_1-C_6)$alkoxy or halogen, and naphtyl-$(C_1-C_6)$-alkyl;

$R_2$ and $R_3$ are each independently hydrogen or halogen;

$R_4$ is a biolabile ester forming group;

and in which the salt is selected from the lithium salt and salts of bivalent metal ions such as magnesium, calcium and zinc. Also described are a method for the preparation of the above salts; pharmaceutical compositions comprising the above salts; methods of using the above salts to treat heart disorders or hypertension, to improve gastrointestinal blood flow, or to treat or inhibit cardiac damage induced by adriamycin and comparable anti-cancer drugs; and crystalline S-α-methylbenzylamine salts of the compounds of formula (I) that are useful as intermediates in production of the above salts.

15 Claims, No Drawings

SOLID SALTS OF BENZAZEPINE COMPOUNDS AND PHARMACEUTICAL COMPOSITIONS CONTAINING THEM

CROSS REFERENCE TO RELATED APPLICATIONS

This application is a continuation of international patent application no. PCT/EP03/00515, filed Jan. 15, 2003 designating the United States of America, and published in English on Jul. 24, 2003 as WO 03/059939 A1, the entire disclosure of which is incorporated herein by reference. Priority is claimed based on European patent application no. EP 02075621.9, filed Jan. 16, 2002, and Netherland patent application no. NL 1019762, filed Jan. 17, 2002.

BACKGROUND OF THE INVENTION

The invention relates to a group of novel salts of compounds with the formula

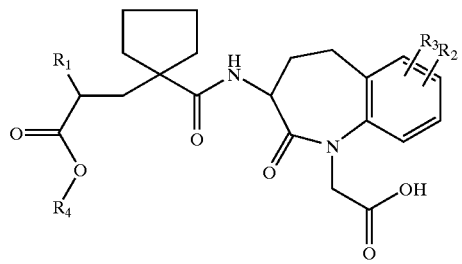

and their use in the preparation of pharmaceutical compounds.

Benzazepines with the above formula are known from EP 0733642, EP 0830863, WO00/48601 and WO01/03699. EP 0733642 is related to compounds with the formula (I) and their physiologically acceptable salts as such and to the use of the compound in heart insufficiency. EP 0830863, WO00/48601 and WO01/03699 are related to the use of the above compounds in the improvement of gastrointestinal blood flow, in the treatment of hypertension and in the treatment and prophylaxis of cardiac damages induced by adriamycin and comparable anti-cancer drugs, respectively.

Preferred benzazepines are the compounds wherein $R_1$ is a phenylethyl group or a 1-naphtylethyl group, $R_2$ and $R_3$ are both hydrogen and wherein $R_4$ is a biolabile ester group. Suitable groups forming biolabile esters include $(C_1-C_6)$-alkyl groups, phenyl or phenyl-$(C_1-C_6)$-alkyl groups which are optionally substituted in the phenyl ring by $(C_1-C_6)$-alkyl or by a $(C_2-C_6)$-alkylene chain bonded to two adjacent carbon atoms, dioxolanylmethyl groups which are optionally substituted in the dioxolane ring by $(C_1-C_6)$-alkyl or $(C_2-C_6)$-alkanoyloxymethyl groups which are optionally substituted on the oxymethyl group by $(C_1-C_6)$-alkyl. Where the group $R_4$ is a by $(C_1-C_6)$-alkyl this is preferably an unbranched $(C_1-C_4)$-alkyl group. In the most preferred compounds $R_4$ is ethyl.

During further pharmaceutical and clinical development it has appeared that the most preferred compounds have the serious draw-back of being a solid foam. In order to ensure a reproducible constant bioavailability of an active ingredient from a solid pharmaceutical dosage form, it is important that a homogeneous and reproducible modification of the active compound is used. Therefore there always exist certain doubts regarding the reproducibility and constantness of bioavailability in compounds that originate from material that normally is not homogeneous, such as a solid foam.

It is also apparent that it is very difficult to isolate a solid foam on a commercial scale. Further the compound is very sparsely soluble in water and therefore it is very difficult to prepare a formulation of the compound that can be used for IV administration. Up to the present invention an IV formulation only could be prepared from the corresponding diacid (see example II in EP 0733642). This means that for an IV formulation another compound has to be used than for an oral formulation, which is undesirable for a pharmaceutical compound. During further development it appeared that the sodium- and potassium salt of the mono acid are much better soluble in water, but these salts can also only be isolated as a solid foam.

SUMMARY OF THE INVENTION

It is an object of the present invention to provide an improved salt of a compound corresponding the formula (I).

Another object of the invention is to provide a salt of a compound corresponding to formula (I) which can be easily isolated in a pure, solid form by by crystallisation or precipitation on commercial production scale.

A further object of the invention is to provide a salt of a compound corresponding to formula (I) which is sufficiently soluble in physiological fluid to enable preparation of an IV formulation.

An additional object of the invention is to provide a salt of a compound corresponding to formula (I) with solid state properties which allow preparation of a pharmaceutical formulation with standard auxiliary compounds and standard equipment.

Yet another object of the invention is to provide a salt of a compound corresponding to formula (I) which can be formulated into a pharmaceutical formulation without substantial loss of chiral and/or chemical purity.

These and other objects have been achieved in accordance with the present invention by providing a salt of a compound corresponding to the formula (I):

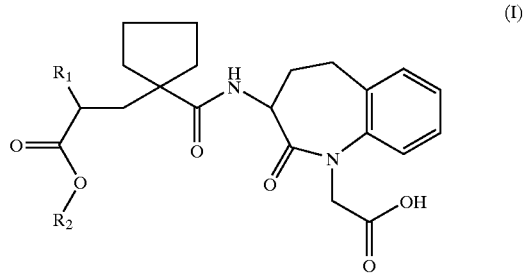

wherein:

$R_1$ is a phenyl-$(C_1-C_6)$-alkyl group or a 1-naphthyl-$(C_1-C_6)$-alkyl group.

$R_2$ is a biolabile ester forming group;

said salt being a pharmaceutically acceptable salt selected from the group consisting of the lithium salt, the calcium salt, the magnesium salt and the zinc salt.

In accordance with a further aspect of the invention, the objects are also achieved by providing a method of preparing a salt of a compound corresponding to the formula (I):

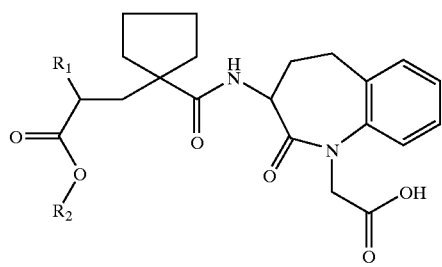

wherein:
R$_1$ is a phenyl-(C$_1$–C$_6$)-alkyl group or a 1-naphthyl-(C$_1$–C$_6$)-alkyl group, and
R$_2$ is a biolabile ester forming group;

said salt being a pharmaceutically acceptable salt of a metal selected from the group consisting of lithium, calcium, magnesium and zinc;

said method comprising mixing a solution or slurry of the hydroxide of said metal with a solution or slurry of the compound of formula I in a slightly polar aprotic solvent to yield a homogeneous solution of the salt in said slightly polar aprotic solvent.

Thus, the invention relates to preparation of a metal salt of a compound corresponding to formula (I), as mentioned above, in which the metal ion is a lithium ion or a bivalent metal ion. Preferred bivalent metal salts are calcium, magnesium and zinc salts. Most preferred is the calcium salt. Surprisingly it has appeared that these salts, contrary to the sodium and potassium salts mentioned in EP0733642 have highly desirable properties, as they can be isolated in solid (amorphous) form and have a solubility in an isotonic fluid of pH 7.4 which is at least a factor of 10 higher than the corresponding acid. Further the bivalent salts can be prepared without racemisation.

Furthermore, in another aspect of the present invention, a method is provided for the preparation of metal salts, preferably Li$^+$ or the bivalent Ca$^{2+}$, Mg$^{2+}$ or Zn$^{2+}$ salts.

It has surprisingly been found that lithium salts and bivalent metal salts of the compound of formula I are very soluble in slightly polar aprotic solvents at room temperature, such as cyclohexane, toluene, methyl tertiairy butyl ether and ethyl acetate.

The salts of the present invention can be easily obtained by mixing the hydroxide or a suitable salt of the desired metal with a solution or slurry of the compound of formula I in one of the above-mentioned slightly polar aprotic solvents. Alternatively, when the hydroxide or salt of the desired metal is not soluble enough to start the reaction, a small amount of water can be added to the solution or slurry in the organic solvent and the water can be removed by azeotropic distillation. In that case an apolar aprotic solvent which forms an azeotrope with water has to be selected. For metals that have a highly insoluble hydroxide the metal can be added in the form of an ethoxide (e.g. Mg(OEt)$_2$) or as a mixed hydroxide/carbonate (3Zn(OH)$_2$.2ZnCO$_3$). The preferred solvent f or the above method is methyl tertiary-butyl ether or e thyl acetate.

When the salt has been obtained in solution it can be isolated by first removing the water that is still available by azeotropic distillation, followed by mixing with a precipitant. A precipitant is defined as a second liquid that is added to a solution to reduce the solubility of the dissolved compound, causing its precipitation/crystallization and maximizing the yield of product. It is necessary for the two liquids (the original solvent and the added precipitant) to be completely miscible with one another in all proportions. (This approach is also used to reduce the solubility of an inorganic salt in aqueous solution by the addition of a water-miscible organic solvent (ALFASSI Z. B. et al., AIChE J. 1984, 30, 874–6; MYDLARZ J. et al., J. Chem. Eng. Data 1989, 34, 124–6; MULLIN J. W. et al., Chem. Eng. Process. 1989, 26, 93–9). Examples of precipitants within the scope of the present invention include linear hydrocarbons. Preferred precipitants are linear C$_4$–C$_{10}$ hydrocarbons. The most preferred precipitant is n-hexane.

As in all cases the salt is isolated in the form of a non-crystalline precipitate, which appears in all cases to be homogeneous, it is sometimes desirable to have a real crystallisation step in order to improve the purity of the active compound which has to meet strict requirements. It has surprisingly been found that the S-α-methylbenzyl amine salt of the compound of formula I is extremely suitable in the purification of these compounds, as said salt is crystalline and can be easily re-crystallized in high yields from organic solvents, preferably alcohols such as ethanol or isopropyl alcohol. Therefore the present invention is also related to S-α-methylbenzylamine salts of the compounds of formula I. The S-α-methylbenzylamine salts are only suitable as intermediates in a purification step, as the S-α-methylbenzylamine cation appears to be too toxic for pharmaceutical use.

The S-α-methylbenzylamine salts of the compounds of formula I can be prepared by adding S-α-methylbenzylamine to a solution of the compound of formula I in ethanol or isopropanol or another suitable alcohol. The salt will crystallize from that solution upon standing and cooling (depending on concentration).

The pharmaceutically acceptable salts of the present invention can be formulated according to state-of-the art formulation processes. Customary formulations can be used, such as, e.g. tablets, capsules or suppositories. These pharmaceutical formulations can be produced by known methods such as direct compression, granulation, extrusion, molding using conventional solid excipients such as fillers e.g. celluloses, lactoses and starches, binders e.g. celluloses and polyvinylpyrrolidon (pvp), desintegrants e.g. starches and cross-linked polyvinylpyrrolidone, glidiants e.g. colloidal silica, lubricants e.g magnesium stearate or conventional liquid and semi-solid excipients such as poly ethylene glycols, caster oil derivates, triglycerides and paraffins. Additionally preservatives e.g. parabens and emulsifiers e.g. poly sorbates can be added.

The pharmaceutically acceptable salts of the present invention are suitable as medicaments for larger mammals, especially humans, for in the treatment of heart failure and for promoting diuresis/natriuresis, especially in patients suffering from heart failure, for the improvement of gastrointestinal blood flow, in the treatment of hypertension and in the treatment and prophylaxis of cardiac damage induced by adriamycin and comparable anti-cancer drugs. For this purpose the compounds of the invention can be used in medicinal forms which can be administered parenterally, especially i.v., orally or as suppository.

The dosages to be used may vary individually and vary with the nature of the condition to be treated, the particular substance used and the mode of administration. Medicinal forms with an active substance content of from 1 to 800 mg per individual dose are generally suitable for administration to larger mammals, especially humans.

The following examples are only intended to further illustrate the invention, in more detail, and therefore these example are not deemed to restrict the scope of the invention in any way.

EXAMPLES

Example 1

General Procedure for the Preparation of Metal Salts of Compounds of Formula 1

About 15 mmole of the active substance in the acid form was solved or suspended in 40 ml of a slightly polar aprotic solvent. A solution of about 1.2 equivalents of the metal reagent in water or in the same solvent as the active compound was added. In some cases water had to be added to start the reaction. The water was removed by azeotropic distillation. When the metal reagent was not a hydroxide or an ethoxide, the solvent was totally removed, followed by re-dissolution in 40 to 160 ml of the original slighly polar aprotic solvent, followed by filtration in order to remove unreacted metal reagent and optional other salts formed. The filtered solution was dosed to hexane and, when a solid product was formed, it was collected on a filter. When a tar or oil was formed the largest part of the solvent was decanted and the remaining solvent was evaporated to yield a solid foam.

TABLE I

Preparation of different salts of two active substances.

| Cmpnd* | Metal in salt | Metal reagent M | Solvent | Amnt of M (g) (mmole) | Amnt of solvent (ml) | Amnt of hexane (ml) | Yld (%) | Result |
|---|---|---|---|---|---|---|---|---|
| I | $Ca^{2+}$ | $Ca(OH)_2$ | MTBE | 0.67 (9.0) | 40 | 80 | 95 | Solid powder |
| I | $Mg^{2+}$ | $Mg(OEt)_2$ | MTBE | 1.25 (10.9) | 40 | 130 | 103 | Solid powder |
| I | $Zn^{2+}$ | $3Zn(OH)_2 \cdot 2Zn(CO_3)_2$ | MTBE | 1.05 (10.9) | 115 | 235 | 95 | Solid powder |
| I | $Li^+$ | LiOH | MTBE | 0.4 (16.7) | 160 | 130 | 85 | Solid powder |
| I | $K^+$ | KOH | MTBE | 1.02 (18.3) | 95 | 235 | 98 | Solid foam |
| I | $Na^+$ | NaOH | MTBE | 1.02 (17.8) | 95 | 235 | 89 | Solid foam |
| II | $Ca^{2+}$ | $Ca(OH)_2$ | EtOAc | 0.56 (7.6) | 75 | 235 | 87 | Solid powder |

*Compound I = 1H-1-Benzazepine-1-acetic acid, 3-[[[1-[(2R)-2-(ethoxycarbonyl)-4-phenylbutyl]cyclopentyl]carbonyl]amino]-2,3,4,5-tetrahydro-2-oxo-, (3S)-.
*Compound II = 1H-1-Benzazepine-1-acetic acid, 3-[[[1-[2-(ethoxycarbonyl)-4-(1-naphthalenyl)butyl]cyclopentyl]carbonyl]amino]-2,3,4,5-tetrahydro-oxo-,[S-(R*,S*)]-.

The properties of the resulting salts are summarized in Table 2. The compound content was determined with an HPLC-method (MACHEREY-NAGEL Nucleosil 100-5 $C_{18}$-HD as a column, using a gradient system starting from 5% B and ending with 100% B, with a phosphoric acid buffer of pH=5.1 as eluent A and eluent B being acetonitril mixed with 10% eluent A). The metal content was determined by a complexometric titration with ethylenediaminetetra-acetic acid disodiumsalt solution for Calcium and with Atomic Emission Spectroscopy (AES) for all other metals.

TABLE 2

Properties of salts prepared according to Table 1.

| Cmpnd* | Metal in salt | Compound content (% rel) | Metal content (% w/w) | Theoretical metal content (% w/w) | Solubility in slightly polar aprotic organic solvents | Solubility in water |
|---|---|---|---|---|---|---|
| I | $Ca^{2+}$ | 99.8 | 3.8 | 3.6 | Soluble | Soluble |
| I | $Mg^{2+}$ | 99.6 | 2.4 | 2.2 | Soluble | Soluble |
| I | $Zn^{2+}$ | 99.9 | 7.0 | 5.8 | Soluble | Soluble |
| I | $Li^+$ | 88.0 | 1.6 | 1.3 | Soluble | Very soluble |
| I | $K^+$ | 78.4 | 7.5 | 6.8 | Not soluble | Very soluble |
| I | $Na^+$ | 84.7 | 4.3 | 4.1 | Not soluble | Very soluble |
| II | $Ca^{2+}$ | n.d. | 3.4 | 3.3 | Soluble | Soluble |

*Compound I = 1H-1-Benzazepine-1-acetic acid, 3-[[[1-[(2R)-2-(ethoxycarbonyl)-4-phenylbutyl]cyclopentyl]carbonyl]amino]-2,3,4,5-tetrahydro-2-oxo-, (3S)-.
*Compound II = Compound II = 1H-1-Benzazepine-1-acetic acid, 3-[[[1-[2-(ethoxycarbonyl)-4-(1-naphthalenyl)butyl]cyclopentyl]carbonyl]amino]-2,3,4,5-tetrahydro-oxo-,[S-(R*,S*)]-.
n.d. = not determined From Table 2 it appears that the Li, Ca, Mg and Zn salts, which were isolated as solid powders, are soluble in slightly polar aprotic solvents. Examples of these solvents include ethyl acetate, toluene, cyclohexane and methyl t-butyl ether. The compounds are also soluble in polar aprotic solvents such as THF, acetone, acetonitril, DMF and DMSO. The metal contents found in the salt are somewhat higher than the theoretical amounts, but this is normal in these types of work-up and analyses. During salt formation with the strongly basic monovalent hydroxides degradation of the active substance occurs, leading to a low compound content in the final salt.

Example 2

Preparation of the S-α-methylbenzylamine salt of 1H-1-Benzazepine-1-acetic Acid, 3-[[[1-[(2R)-2-(ethoxycarbonyl)-4-phenylbutyl]-cyclopentyl]carbonyl]amino]-2,3,4,5-tetrahydro-2-oxo-, (3S)

18 g of 1H-1-Benzazepine-1-acetic acid, 3-[[[1-[(2R)-2-(ethoxycarbonyl)-4-phenyl-butyl]cyclopentyl]carbonyl]amino]-2,3,4,5-tetrahydro-2-oxo-, (3S)- were dissolved in 90 ml of absolute ethanol. 4.1 g S-methylbenzyl amine was added at 20–25° C. The spontaneously formed crystal slurry was heated to 40° C. and stirred for one hour. After cooling to 0–5° C. and additional stirring for 4 hours, the crystals were collected by filtration, washed with 40 ml chilled absolute ethanol, and dried at 45° C. in a vacuum oven. 19 g of the S-methylbenzyl amine salt of 1H-1-Benzazepine-1-acetic acid, 3-[[[1-[(2R)-2-(ethoxycarbonyl)-4-phenylbutyl]cyclopentyl]carbonyl]amino]-2,3,4,5-tetrahydro-2-oxo-, (3S)- were yielded as first crop.

Example 3

Preparation of the calcium salt of 1H-1-Benzazepine-1-acetic acid, 3-[[[1-[(2R)-2-(ethoxycarbonyl)-4-phenylbutyl]cyclopentyl]carbonyl]amino]-2,3,4,5-tetrahydro-2-oxo-, (3S)

To a solution of 30 g of the S-α-methylbenzylamine salt of 1H-1-Benzazepine-1-acetic acid, 3-[[[1-[(2R)-2-(ethoxycarbonyl)-4-phenylbutyl]cyclopentyl]carbonyl]-amino]-2,3,4,5-tetrahydro-2-oxo-, (3S)- in 120 ml of methyl tertiary-butyl ether (MTBE), 100 ml of a 1M aqueous solution of hydrochloric acid was added and the resulting mixture was stirred for 10 minutes. The layers were separated, and the organic layer was washed at least three times with 15 ml portions of water until the pH was higher than 5. An amount of 2 g Ca(OH)$_2$ 95% was added, and the mixture was heated to 55° C. under reflux. When the amount of suspension was not significantly diminished after 30 minutes, an amount of 0.5 ml of water was added. The mixture was refluxed via a water trap (Dean-Stark apparatus) over the course of 2 hours. After 2 hours the distillate was completely clear and the reaction mixture was a little bit turbid. The mixture was cooled to 30–35° C. and introduced over the course of 30 minutes via an in-line filter into 240 ml of hexane. The resulting solid product was isolated by filtration and washed with 50 ml of hexane. After drying, 25.6 g of an off-white, free flowing powder was obtained.

$^1$H-NMR: δ=7.29 (1H, dd, J=2.2 and 8.1), 7.28 (1H, ddd, J=2.0, 6.6, 8.1), 7.25 (1H, dd, J=2.0 and 7.6), 7.19 (1H, ddd, J==2.2, 6.6, 7.6), 7.19 (2H, dddd, J=0.6, 1.7, 7.5, 7.8), 7.13 (1H, dd, J=1.3 and 7.5), 7.10 (2H, ddd, J=1.3, 2.1, 7.8), 4.39 (1H, d, J=16.9), 4.28 (1H, dd, J=8.1 and 11.7), 4.28 (1H, d, J=16.9), 4.07 (1H, dd, J=7.2 and 10,8), 4.01 (1H, dd, J=7.1 and 10.8), 3.33 (1H, ddd, J=8.0, 13.2, 13.7), 2.57 (1H, ddd, J=1.2, 7.1, 13.7), 2.52 (1H, dd, J=5.9 and 9.6), 2.49 (1H, dd, J=6.7 and 9.4), 2.31 (1H, dddd, J=3.3, 5.1, 9.2, 9.3), 2.29 (1H, dddd, J=7.1, 8.1, 13.1, 13.2), 2.03 (1H, dddd, J=1.2, 8.0, 11.7, 13.1), 2.0 (1H, dd, J=9.3 and 14.2), 1.82 (1H, dd, J=3.3 and 14.2), 1.82 (1H, ddd, J=5.9, 9.4, 13.6), 1.70 (1H, ddd, J=6.7, 9.6, 13.6), 2.02–1.42 (8H, m), 1.21 (3H, dd, J=7.1 and 7.2)

Example 4

Preparation of the S-α-methylbenzylamine salt of Compound II=1H-1-Benzazepine-1-acetic acid, 3-[[[1-[2-(ethoxycarbonyl)-4-(1-naphthalenyl)-butyl] cyclopentyl]carbonyl]amino]-2,3,4,5-tetrahydro-oxo-,[S-(R*,S*)]

21 g of Compound II=1H-1-Benzazepine-1-acetic acid, 3-[[[1-[2-(ethoxycarbonyl)-4-(1-naphthalenyl)butyl]cyclopentyl]carbonyl]amino]-2,3,4,5-tetrahydro-oxo-,[S-(R*,S*)]- were dissolved in 190 ml of MTBE. 45 ml of ethanol and 4.5 g S-α-methylbenzyl amine were added. After storage for 4 days at 4° C. and stirring once a day, the crystals were collected by filtration, washed with 80 ml MTBE and dried at 45° C. in a vacuum oven. 19 g of the S-methylbenzyl amine salt of Compound II=1H-1-Benzazepine-1-acetic acid, 3-[[[1-[2-(ethoxycarbonyl)-4-(1-naphthalenyl)butyl] cyclopentyl]carbonyl]-amino]-2,3,4,5-tetrahydro-oxo-,[S-(R*,S*)]-. were yielded as first crop.

Example 5

Preparation of the calcium Salt of 1H-1-Benzazepine-1-acetic acid, 3-[[[1-[2-(ethoxycarbonyl)-4-(1-naphthalenyl)-butyl]cyclopentyl]carbonyl]-amino]-2,3,4,5-tetrahydro-oxo-,[S-(R*,S*)]

To a heterogeneous mixture of 10 g of the S-α-methylbenzylamine salt of 1H-1-Benzazepine-1-acetic acid, 3-[[[1-[2-(ethoxycarbonyl)-4-(1-naphthalenyl)-butyl]-cyclopentyl] carbonyl]amino]-2,3,4,5-tetrahydro-oxo-,[S-(R*,S*)]- in 80 ml of methyl tertiary-butyl ether (MTBE) and 60 ml of water, 4.4 ml of a 36% aqueous solution of hydrochloric acid were added over the course of 15 minutes under stirring, and the resulting mixture was stirred for 1.5 hours at room temperature. The layers were separated, and the organic layer was washed two times with 50 ml portions of water. The organic layer was concentrated to an oil, 15 ml of ethyl acetate was added, and the solution obtained was again concentrated to an oil. The oil was dissolved again in 80 ml of ethyl acetate, and 2 ml of water were added. An amount of 0.56 g Ca(OH)$_2$ 95% was added, and the mixture was refluxed over the course of 4 hours via a water trap (Dean-Stark apparatus). The solution was filtered and reduced in volume to 40 ml. The solution was cooled to 30–35° C.; introduced over the course of 30 minutes into 250 ml of cold hexane (10° C.), and stirred for an additional 30 minutes at 10° C. The resulting solid product was isolated by filtration and washed twice with 10 ml portions of hexane. After drying under vacuum (18 hours, 50° C., 120 mbar), 7.4 g of free flowing powder was obtained.

$^1$H-NMR: δ=7.99 (1H, broad doublet, J=8), 7.88 (1H, dd, J=1.5 and 8), 7.73 (1H, broad doublet, J=8), 7.56–7.44 (2H, m), 7.37 (1H, t, J=8), ~7.36 (NH, d, J=8), 7.31 (1H, dd, J=1.5 and 8), 7.29 (1H, d, J=8), 7.24 (1H, triple doublet, J=1.5, 8, 8), 7.21 (1H, dd, J=1.5 and 8), 7.13 (1H, triple doublet, J=1.5, 8, 8), 4.48(1H, d, J=16), 4.23 (1H, double triplet, J=8, 8.12), 4.14–3.99 (3H, m), 3.56 (1H, triple doublet, J=8, 13, 13), 3.02–2.96 (2H, m), 2.5–2.34 (2H, m), 2.2–1.74 (8H, m), 1.6–1.24 (6H, m), 1.20 (3H, t, J=6).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pharmaceutically acceptable salt selected from the group consisting of the lithium, calcium, magnesium and zinc salts of 3-[[[1-[(2R) -2-(ethoxycarbonyl)-4-phenylbutyl]cyclopentyl]carbonyl]amino]-2,3,4,5-tetrahydro-2-oxo-(3S)-1H-1-benzazepine-1-acetic acid, and the calcium salt of 3-[[[1-[2-(ethoxycarbonyl)-4-(1-naphthalenyl)butyl]cyclopentyl]carbonyl]amino]-2,3,4,5-tetrahydro-oxo-,[S-(R*, S*)]-1H-1H-1-benzazepine-1-acetic acid.

2. A salt according to claim 1, wherein said salt is a calcium salt.

3. A method of preparing a salt

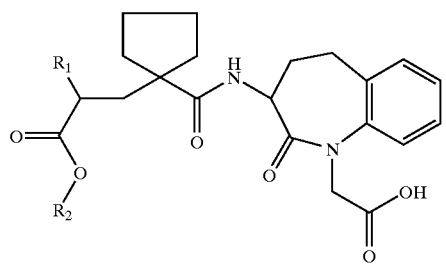

according to claim 1; said method comprising mixing a solution or slurry of the hydroxide of lithium, calcium, magnesium or zinc with a solution or slurry of 3-[[[1-[(2R)-2-(ethoxycarbonyl)-4-phenylbutyl]cyclopentyl]carbonyl]-amino]-2,3,4,5-tetrahydro-2-oxo-(3S)-1H-1-benzazepine-1-acetic acid, or a solution or slurry of calcium hydroxide with a solution or slurry of 3-[[[1-[2-(ethoxycarbonyl)-4-(1-naphthalenyl)butyl]cyclopentyl]carbonyl]amino]-2,3,4,5-tetrahydro-oxo-,[S-(R*,S*)]-1H-1H-1-benzazepine-1-acetic acid, in a slightly polar aprotic solvent to yield a homogeneous solution of the salt in said slightly polar aprotic solvent.

4. A method according to claim 3, wherein said slightly polar aprotic solvent is methyl tertiary-butyl ether or ethyl acetate.

5. A method according to claim 3, further comprising isolating said salt by mixing the solution of the salt in the slightly polar aprotic solvent with a precipitant to crystallize or precipitate the salt in solid form.

6. A method according to claim 5, wherein the mixing with the precipitant is preceded by azeotropic removal of water.

7. A method according to claim 5, wherein said precipitant is a linear ($C_4$–$C_{10}$)-hydrocarbon.

8. A method according to claim 7, wherein said precipitant is n-hexane.

9. A pharmaceutical composition comprising at least one salt according to claim 1 and a pharmaceutical carrier or adjuvant.

10. A composition according to claim 9, wherein said composition is in a form suitable for IV administration.

11. A method of treating a heart disorder in a patient, said method comprising administering to a patient in need thereof an effective heart disorder treating amount of a salt according to claim 1.

12. A method of improving gastrointestinal blood flow in a patient, said method comprising administering to a patient in need thereof an effective gastrointestinal blood flow improving amount of a salt according to claim 1.

13. A method of treating hypertension, said method comprising administering to a patient in need thereof an effective hypertension treating amount of a salt according to claim 1.

14. A method of treating or inhibiting cardiac damage induced by a cardiac damage inducing anti-cancer drug, said method comprising administering to a patient treated with said anti-cancer drug an effective cardiac damage inhibiting amount of a compound according to claim 1.

15. A method according to claim 14, wherein said anti-cancer drug is adriamycin.

* * * * *